(12) United States Patent  
Brewer

(10) Patent No.: US 7,708,709 B2
(45) Date of Patent: *May 4, 2010

(54) ORTHOTIC PROTECTIVE DEVICE

(76) Inventor: Jeffery L. Brewer, 1417 Shelton Dr., Nacogdoches, TX (US) 75965

( * ) Notice: Subject to any disclaimer, the term of this patent is extended or adjusted under 35 U.S.C. 154(b) by 0 days.

This patent is subject to a terminal disclaimer.

(21) Appl. No.: 12/176,953

(22) Filed: Jul. 21, 2008

(65) Prior Publication Data
US 2009/0018477 A1 Jan. 15, 2009

Related U.S. Application Data

(63) Continuation of application No. 10/623,271, filed on Jul. 15, 2003, now Pat. No. 7,402,148.

(60) Provisional application No. 60/395,801, filed on Jul. 16, 2002.

(51) Int. Cl.
A61F 5/00 (2006.01)
(52) U.S. Cl. .......................................... 602/21; 602/20
(58) Field of Classification Search ................... 602/16, 602/20, 21, 64
See application file for complete search history.

(56) References Cited

U.S. PATENT DOCUMENTS 4,666,158 A * 5/1987 Moro ........................... 473/62
6,080,121 A 6/2000 Madow
6,165,148 A 12/2000 Carr-Stock
6,186,969 B1 2/2001 Bell
6,279,159 B1 8/2001 Ahlbaumer
6,443,918 B1 * 9/2002 Wang ............................ 602/5
6,540,710 B1 4/2003 Cruz

* cited by examiner

Primary Examiner—Patricia M Bianco
Assistant Examiner—Camtu T Nguyen
(74) Attorney, Agent, or Firm—Browning Bushman P.C.

(57) ABSTRACT

An orthotic protective device collectively including a base unit connected to a metacarpal unit by a hinge system designed to protect and prevent hyperextension and hyperflexion movements of the metacarpal, carpal, radius and ulna regions. The base unit and metacarpal unit includes a longitudinal support member and a casing, respectively, lined with at least one pad having a tongue. At least one releasable fastener is mated to the support member and casing and extends to the tongue of the pad.

Apertures of the base unit are mated and connected to apertures of the hinge system which form an articulated joint allowing the hinge system to move in an upward manner allowing for natural extension of the user's wrist and in a downward fashion for unlimited flexion motion. The base unit and the hinge system may both have at least one stop formed thereon; and as these stops come into contact with one another, it limits the flexion, extension and radial-ulnar deviation. Further, an aperture of the metacarpal unit is mated and fastened to an aperture in the hinge system by a swivel joint which allows for lateral movement of the user's wrist.

19 Claims, 3 Drawing Sheets

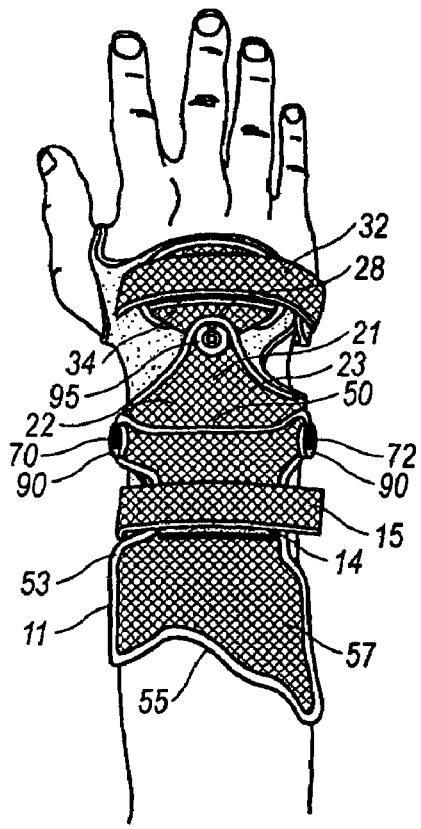
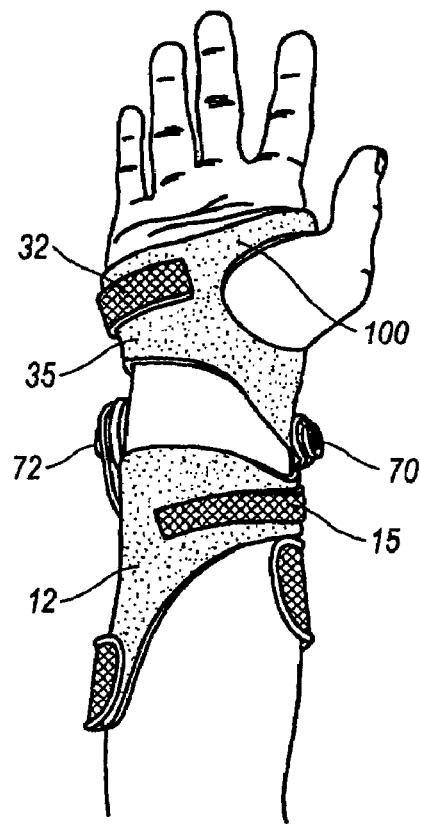
FIG. 3      FIG. 4
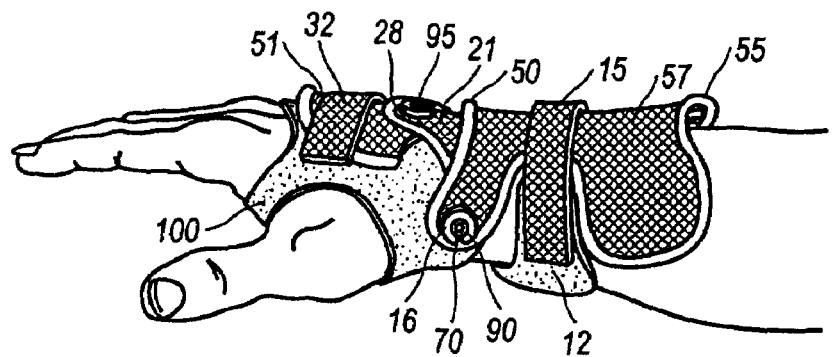
FIG. 5
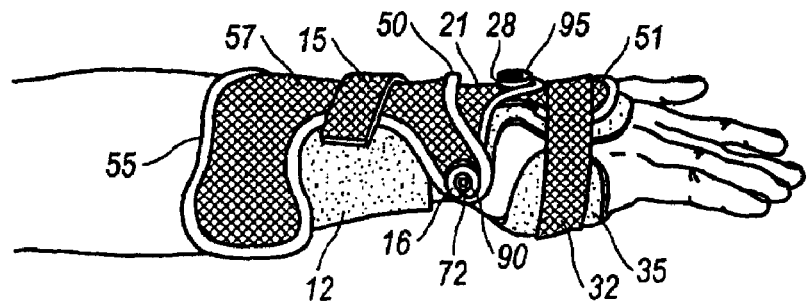
FIG. 6

ORTHOTIC PROTECTIVE DEVICE

PRIOR APPLICATIONS

This application claims the benefit of Provisional Patent Application Ser. No. 60/395,801 filed on Jul. 16, 2002.

This application is a continuation of Ser. No. 10/623,271 filed Jul. 15, 2003, now U.S. Pat. No. 7,402,148.

TECHNICAL FIELD

The present invention relates generally to an orthotic protective device, more particularly a brace for the metacarpals, carpals, radius and ulna regions and method of providing the same which provides for normal movement of a user.

BACKGROUND OF THE INVENTION

A wide range of activities such as playing a musical instrument, playing golf, opening a bottled drink or even laying bricks are all impossible activities to execute without the health of a user's arm, wrist and hands. Nevertheless, these physiological areas are most prone to injury in the human body.

Today, a number of physical therapists and physicians deal with two major types of injuries: (1) repetitive motion injuries and (2) traumatic injuries. The repetitive motion injuries develop over a period of time where consistent use of the arms, wrists and hands are required, such as assembly line tasks. Such repetitive motion injuries are treated by developing plans to address muscle and joint stress and weakness and redesigning workstations, tools and equipment.

However, traumatic injuries such as fractures and lacerations require immediate medical care. One type of traumatic injury is a sprain which can take weeks to heal properly. A physician or therapist focuses on restoring strength and mobility and on preventing the creation of adverse scar tissue which can permanently affect the function of the hand, wrist or any joint.

Another type of traumatic injury is the result of sporting accidents, such as inline skating accidents. Here, if a sporting enthusiast falls on his/her outstretched hand, the enthusiast may suffer a Colles' fracture, a fracture of the bones of the forearm (the radius and the ulna) near the wrist (or carpal bones). In order to prevent such an injury from occurring, the enthusiast should wear protective gear including wrist protectors.

Examples of such a device is depicted in U.S. Pat. No. 6,165,148 (hereinafter called '148) issued to Carr-Stock on Dec. 26, 2000. The '148 patent provides for a wrist/hand/finger orthosis having a splint member extending from forearm to fingertips, a cover enclosing the splint member and a plurality of releasable straps connected to the cover.

An advancement in the orthotic industry was to combine elastic and non-elastic fabric in the construction of wrist braces. An example of a device incorporating these fabrics is depicted in U.S. Pat. No. 6,186,969 (hereinafter called '969) issued to Bell on Feb. 13, 2001. The '969 patent is a wrist brace having a sheet of flexible material having a first portion which is substantially non-stretchable and a second portion which is stretchable. The first and second portions allow the brace to vary the compression on the proximal portion of the wrist which is sought to be immobilized.

Protection aids for hands and wrists have continued to develop as is evident with U.S. Pat. No. 6,279,159 (hereinafter called '159) issued to Ahlbaumer on Aug. 28, 2001. The '159 patent describes a hand and wrist protective aid comprising a first protective element to be arranged on the region of the hand palm situated near the wrist. A second protective element is arranged on the inside portion of the wrist and is connected to the first protective element via a connecting element. However, the forearm of a user is left exposed and unprotected.

In 2003, a wrist brace was designed to fixedly link a user's hand to a user's forearm in a rigid fashion whereby the wrist is held in a relatively neutral position as seen in U.S. Pat. No. 6,540,710 issued to Cruz on Apr. 1, 2003. The '710 patent provides for a brace, namely a one-piece unit designed to fit on top of the hand and forearm.

Aside from the physical structure of the brace, other developments have involved the evolution of the materials. An example of this enhanced material is taught in U.S. Pat. No. 6,080,121 (hereinafter called '121) issued to Madow on Jun. 27, 2000. The '121 patent describes a laminated orthopedic brace made of a unique blend of material combining Airprene™ with Coolmax™ material as a liner. This material blend allowed for breathability, compression and heat retention.

SUMMARY OF THE INVENTION

The present invention in its several disclosed embodiments alleviates the drawbacks described above with respect to orthotic devices and incorporates several additionally beneficial features. The present invention described herein is an orthotic protective device, namely a brace to protect and prevent hyperextension and hyperflexion movements of the metacarpal, carpal, radius and ulna regions. The orthotic protective device generally includes a hinge system located between a base unit and a metacarpal unit. The base unit includes a longitudinal support member and the metacarpal unit includes a casing. Each unit is lined with at least one pad having a tongue. At least one releasable fastener is mated to the support member and casing and extends to the tongue of the pad. The tongue of the pad which is connected to the casing has a digit opening to accommodate the digit and is connected to an attachment means.

Apertures of the base unit are mated and connected to apertures of the hinge system which form an articulated joint allowing the hinge system to move in an upward manner allowing for natural extension of the user's wrist and in a downward fashion for unlimited flexion motion. The base unit and the hinge system may both have at least one stop formed thereon; and as these stops come into contact with one another, it limits the flexion, extension and radial-ulnar deviation. Further, an aperture of the metacarpal unit is mated and fastened to an aperture in the hinge system by a swivel joint which allows for lateral movement of the user's wrist.

Another benefit of the present invention is for each pad, such as the support pad(s), interior pad and internal pad, may include cooling and/or heating coils embedded within each pad to either provide the user a cooling or heated effect to reduce swelling and provide relief.

It is therefore a goal of the present invention to provide an orthotic protective device designed to prevent and treat injuries namely for the carpal joint, but also for the metacarpal bones, radius and ulna regions. The orthotic protective device permits normal flexion and extension of the carpal joint while simultaneously preventing involuntary hyper-flexion and hyperextension of this joint.

Another advantage of the present invention is to provide the orthotic device to be worn prophylactically to protect the carpal joint and its surrounding areas from external contact such as blows and impact injury, including but not limited to bodily, equipment or object impact. Further, the orthotic device is easy to manufacture and may be utilized for both personal and commercial uses.

Additionally, the support member may be formed as a one-piece unit or as a segmented body allowing physiological options for the user. The support member may be made of various materials such as thermoplastic material which may be mass produced or customized to fit a particular individual.

Further advantages of the invention will be more clearly understood from the following description of illustrative embodiments thereof, to be read by way of example and not of limitation in conjunction with the apparatus and method shown. The beneficial effects described above apply generally to exemplary devices disclosed herein of the orthotic protective device. The specific structures through which these benefits are delivered will be described in detail herein below.

BRIEF DESCRIPTION OF THE DRAWINGS

The invention will now be described in greater detail in the following way of example only and with reference to the attached drawings, in which:

FIG. 3 is a plan view of the present invention depicting the device worn on a user and extending from the forearm to the hand.

FIG. 4 is a bottom view of the present invention.

FIG. 5 is a left side view of the present invention.

FIG. 6 is a right side view of the present invention.

MODE(S) FOR CARRYING OUT THE INVENTION

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention. Although those of ordinary skill in the art will readily recognize many alternative embodiments, especially in light of the illustrations provided herein, this detailed description is exemplary of the preferred embodiment of the present invention, the scope of which is limited only by the claims appended hereto.

Anatomy of the Hand, Wrist and Forearm

The elbow is a hinge joint connecting the upper arm bone (humerus) with the bones of the forearm (the radius and the ulna). Specifically, the elbow consists of three joints enclosed within a capsule and held together by muscles, tendons, and ligaments. Tendons are fibrous cords that attach muscles to bones; and ligaments are bandage-like sheaths of fibrous tissues that attach bones to bones and keep the joints and bones in alignment.

Unlike the elbow, the wrist and hand are more complex in structure. There are eight wrist bones known as carpals which support the carpal tunnel which contains tendons and the median nerve and is covered by a transverse carpal ligament.

In the hand, the metacarpal bones form the structure of the hand itself and are connected to the finger bones (the phalanges). There are three phalanges in each finger and each finger is supplied with two types of tendons: an extensor tendon on top, which straightens the finger, and a flexor tendon on the bottom, which bends the finger. Interphalangeal joints are the joints between different sections of the finger and metacarpal phalangeal joints connect the fingers to the hand.

The Invention

FIGS. 1-8 illustrate an orthotic protective device 5, namely a brace to protect and prevent hyperextension and hyperflexion movements of the metacarpal, carpal, radius and ulna regions and provide normal pitch and yaw movements of a user. The orthotic protective device 5 collectively includes a hinge system 20 positioned between a base unit 10 and a metacarpal unit (also known as the hand unit) 30.

Figure 1:
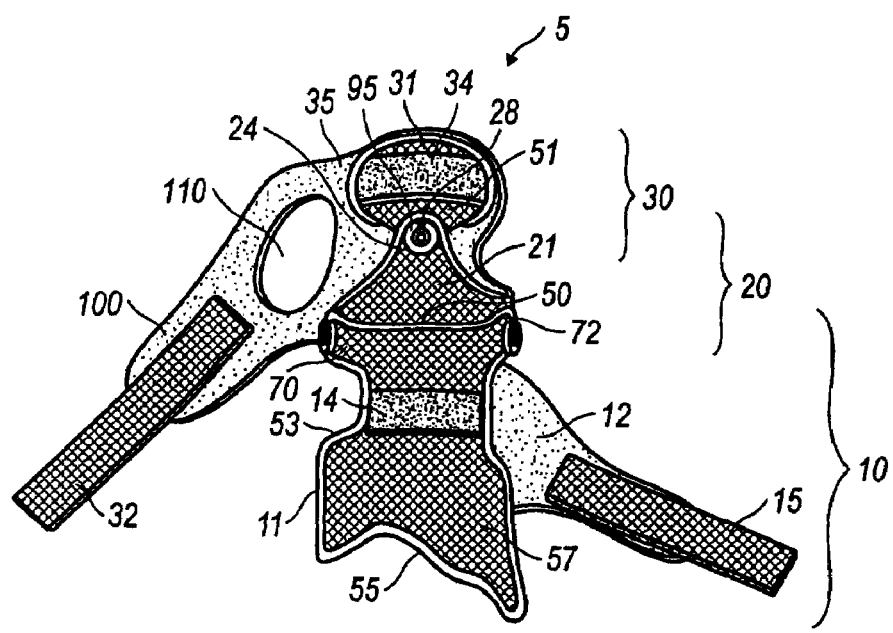
FIG. 1 is a top plan view of an orthotic protective device having a hinge system allowing for movement of a patient's wrist.
Figure 2:
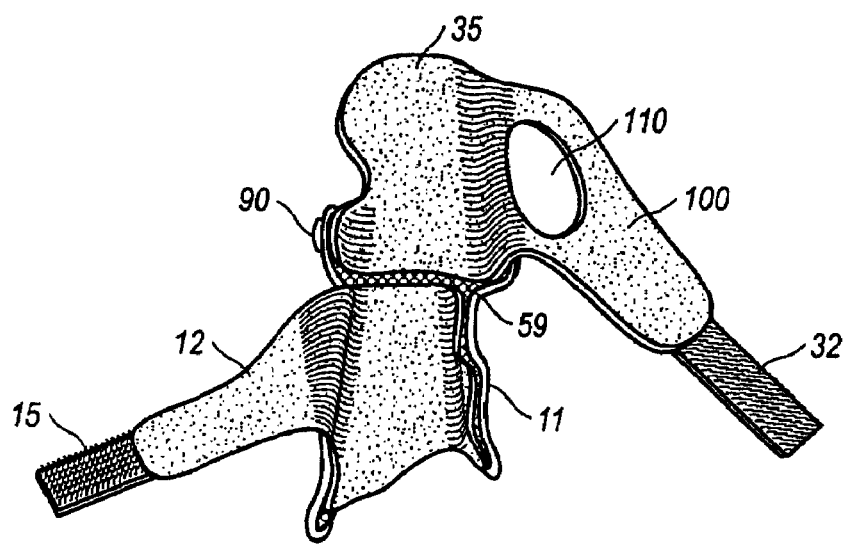
FIG. 2 is a bottom plan view showing an interior surface of the present invention.

FIGS. 1 and 2 show the base unit 10 incorporates a substantially rigid, elongated support member 11 including an interior surface 59 and an exterior surface 57 having a distal end 50, a middle region 53 and a proximate end 55. The elongated support member 11 is preferably shaped as an inverted "U" capable of being positioned on a dorsal side of the radius-ulna region of the user and substantially surrounds and conforms to the user's forearm to ensure a secure fit as seen in FIGS. 3 and 4. Here, the support member 11 may either be formed as a one-piece unit; or alternatively, as a segmented body where each segment is joined to one another to adapt to the user's specific body specifications. The support member 11 may be made of, but not limited to, such materials as moldable carbon fiber, epoxy matrix carbon fiber, KEVLAR™ (aramid fiber) composite material, hard plastic or thermoplastic material which may be mass produced as an off-the-shelf item or customized to fit a particular individual.

FIG. 2 shows the interior surface 59 of the elongated support member 11 is lined with at least one or more support pad(s) 12 attached therein. The support pad(s) 12 and internal pad 35 may be fastened to the interior surface 59 by, but not limited to, hook and loop material such as Velcro™, adhesive, pins, screws, buttons and the like. The support pad(s) 12 may contour a substantial portion or entire surface area of the interior surface 59. In the most preferred embodiment, the support pad 12 has a tongue which projects beyond the surface area of the interior surface 59 and is designed to extend around the volar surface of the radius-ulna region.

At least one releasable fastener 14 is coupled to the exterior surface 57 of the elongated support member 11, preferably on the middle region, 53 as depicted in FIGS. 3, 5 and 6. The releasable fastener 15, preferably a strap, may be fastened to the exterior surface 57 by, but not limited to, Velcro™, adhesive, pins, screws, buttons, nuts, bolts and the like. Specifically, a first end of the releasable fastener 15 is mounted, preferably to a hook and loop patch 14 adhered onto the exterior surface 57 of the support member 11. A second end of the releasable fastener 15 orthogonally extends from the exterior surface 57 and is attached to the tongue of the support pad 12.

The middle region 53 of the exterior surface 57 is adjacently positioned to the proximate end 55 and is positioned across the radius-ulna region. Desirably, the proximate end 55 may be asymmetrically configured to impart comfort and prevent a feeling of confinement to the user. The distal end 50 is also located adjacent to the middle region 53 and is near and extends across the carpal region.

The distal end 50 has opposing sides 70, 72, where each side includes an aperture 16 bored through the support member 11 and capable of receiving connectors 90 therein. Each aperture 16 has a reinforcement perpendicularly extending therefrom designed to surround and support the connectors 90 inserted through the apertures 16.

The hinge system 20 comprises a shell 21 having polar extended sides 22, 23 and a lip 24. An interior pad 35 is removably attached underneath the polar extended sides 22, 23 thereby providing comfort to the carpal region of the user. Each polar extended side 22, 23 has an aperture 28 capable of accepting fasteners therein. These apertures 28 directly correspond to and are positioned underneath the apertures 16 of the support member 11 in order to accept the inserted connectors 90.

Figure 7:
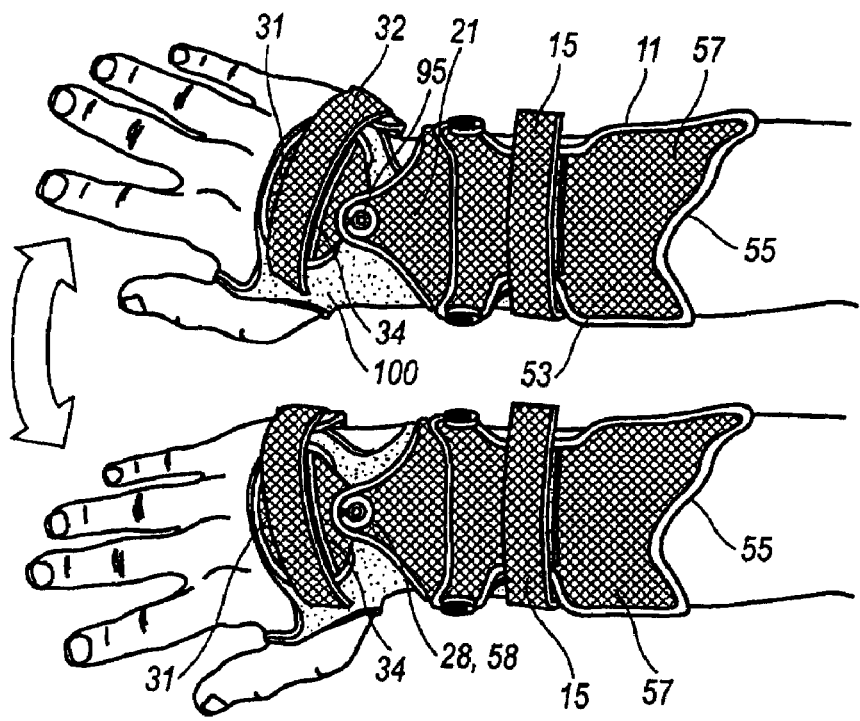
FIG. 7 is a top plan view of the present invention depicting the lateral swivel capabilities of the hinge system.
Figure 8:
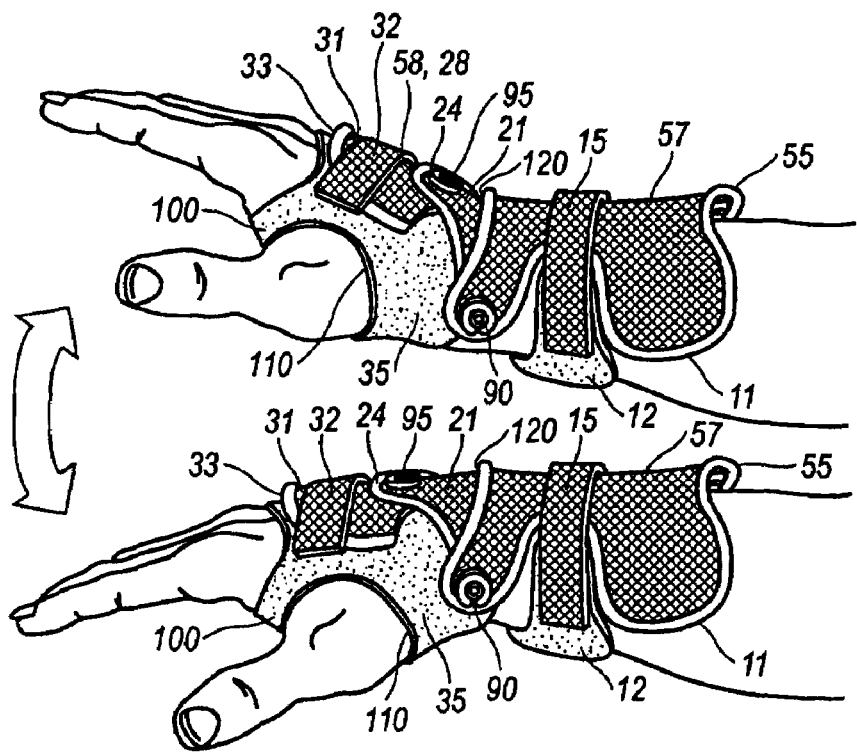
FIG. 8 is a side view of the present invention depicting the user's wrist extending from a horizontal position to a normal flexion position.

The connected apertures 16, 28 form an articulated joint allowing the hinge system 20 to move at about a 45° angle in an upward vertical manner or until the hinge system 20 abuts the base unit 10, thereby limiting the extension of the carpal area specific to the user's maximum range of motion as seen in FIG. 7. FIG. 8 depicts the articulated joint having no flexion resistance.

Operatively speaking, the joint may be flexed at about a 150° angle in a downward manner only limited by the user's natural range of motion. In an alternative embodiment, the angle of the articulated joint may be severely limited by incorporating stops 120 on both the shell 21 and the support member 11 to limit extension, flexion and ulnar-radial deviation. As each stop abuts one another, the range of motion is inhibited.

The orthotic protective device 5 undergoes a scanning and molding process, namely by first scanning and measuring a user's physiological specifications; and then translating the measurements into a mold. The mold is then fabricated by utilizing a wet lay-up process using a combination of epoxy resin, carbon fiber and KEVLAR™ (aramid fiber) composite materials. This process allows for normal movement of the carpal region. The resulting protective device 5 is designed to limit both extension and flexion of the carpal region specific to the patient's maximum range of motion. Further, during the scanning, molding and fabrication process, the stops 120 are formed onto the shell 21 and the support member 11 thereby limiting the user's movement, both natural and hyperextended/hyperflexed movements, as shown in FIG. 8.

The lip 24 has an aperture 28 designed to receive a swivel joint 95 or other connector. The aperture 28 preferably has a reinforcement orthogonally projecting therefrom and surrounding the swivel joint 95 or alternate connector.

The metacarpal unit 30 incorporates a casing 31 including an internal surface 50, and an external surface 51 having an anterior end 52 and a posterior end 54. An internal pad 35 has a tongue 100 and is removably connected to the internal surface 50 of the casing 31, preferably by a hook and loop means. Here, either a hook or loop patch is fastened to the internal surface 50 and is adapted to accept the internal pad 35 as the loop or hook, respectively, are mated. The internal pad 35 substantially conforms to the surface area of the internal surface 50 and the tongue 100 projects outwardly and is designed to extend around the volar surface of the user's palm. The tongue 100 has a digit, namely a thumb, orifice 110 allowing the digit to be inserted therethrough.

A first end of an attachment means 32, namely a strap, is fastened to the casing 31, preferably by a hook and loop connector being adhered to the external surface 51 of the casing 31. The attachment means 32 has the corresponding loop or hook patch, respectively, used to join to the former patch. A second end extends transversely across the external surface and orthogonally extends from the external surface 51 of the casing 31 and is attached to the tongue 100 of the internal pad 35.

Each pad, namely the support pad(s) 12, interior pad 26 and internal pad 35 are resistently compressible, high surface-friction pads designed to secure the orthotic protective device 5 to the user. The pads 12, 26 and 35 may be made from such materials as, but not limited to, open cell foam, closed cell foam, viscoelastic polymer-gel, cotton, liquid material, granular material or air material. In the most preferred embodiment, each pad 12, 26, 35 may include cooling and/or heating coils 42 embedded within each pad 12, 26, 35 to either provide the user a cooling or heated effect to reduce swelling and provide relief. These coils 42 are electrically connected to a temperature control means 40 which may be manipulated by the user to produce a desired effect.

The posterior end of the casing 31 has an aperture 58 which corresponds to the aperture 28 located on the lip 24 of the shell 21. The swivel joint 95 or other connector is accepted by both apertures 28, 58 alike and provides for the metacarpal unit 30 to move in a lateral fashion with respect to the hinge system 20. Specifically, the swivel joint 95 allows up to a 60° turn on each side of its horizontal axis providing for normal movement of the carpal region. In a preferred embodiment, the swivel joint 95, as well as the connectors 90 may comprise of quick release pins allowing for each addition or subtraction of either the base unit 10, metacarpal unit 30 or other accessory or accessories adapted to fit thereto. The substantially rigid casing 31 is preferably positioned over the dorsal surface of the user's hand, and the substantially rigid shell 21 is similarly positioned over the top surface of the user's forearm, as shown in the figures. Further, in a preferred embodiment, the casing 31 and the shell 21 may be made of such materials as, but not limited to, moldable carbon fiber, epoxy matrix carbon fiber, KEVLAR™ (aramid fiber) composite material, hard plastic or thermoplastic material which either being mass produced or having a more customized fit for an individual.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. Therefore, the foregoing detailed description should not be construed as a limitation of the scope of the present invention, which is limited only by the claims appended hereto. The invention is, therefore, claimed in any of its forms or modifications within the proper scope of the appended claims appropriately interpreted in accordance with the doctrine of equivalents.

INDUSTRIAL APPLICABILITY

The present invention finds specific industrial applicability in the medical and athletic industries.

What is claimed and desired to be secured by Letters Patent is as follows:

1. An orthotic device to be worn by a user, comprising:
  a base unit including a support member conforming substantially about a forearm of the user, and a support pad on the support member;

a metacarpal unit including a casing and a metacarpal pad on said casing the metacarpal unit for positioning on the dorsal surface of the user's hand;

a hinge system including a shell extending between the base unit and the metacarpal unit, and a pair of vertical pivot connectors for movably connecting the shell to the base unit when worn by the user, such that the shell pivots vertically about the pair of connectors in a first direction relative to the base unit when worn by the user, the hinge system further including a lateral connector for movably connecting the metacarpal unit to the shell when worn by the user, such that the metacarpal unit pivots with respect to the shell laterally about the lateral connection in a second direction substantially transverse to the first direction when worn by the user, and wherein said support member and said shell each have at least one stop formed thereon, wherein each of said stop abuts one another to limit vertical movement of the support member relative to said shell.

2. The orthotic device as recited in claim 1, wherein said support member, said shell and said casing are each made of a material selected from the group consisting of epoxy matrix carbon fiber, moldable carbon fiber, aramid fiber composite material, plastic and thermoplastic material.

3. The orthotic device as recited in claim 1, wherein said support pad, and said metacarpal pad being made of a material selected from a group consisting of open cell foam, closed cell foam, cotton, a viscoelastic polymer-gel and an air filled member.

4. The orthotic device as recited in claim 3, wherein said support pad is detachably affixed on said support member, said metacarpal pad is detachably affixed on said casing, and said metacarpal pad is detachably fastened on said shell.

5. The orthotic device as recited in claim 1, wherein said metacarpal pad removably positioned on said shell.

6. The orthotic device as recited in claim 1, wherein said hinge system is capable of moving said shell to a 45° angle in a vertical extension fashion with respect to the base unit.

7. The orthotic device as recited in claim 1, wherein said hinge system is capable of moving said shell to a 150° angle in a vertical, flexing fashion with respect to the base unit.

8. An orthotic device for rehabilitation of a user's wrist, comprising:

a base unit having a support member conforming substantially to a forearm of the user;

a metacarpal unit including a casing and a pad and a casing retainer under the dorsal surface of the user's hand for retaining the casing on the dorsal surface of the hand when worn by the user;

a hinge system movably connecting the metacarpal unit to the base unit when worn by the user, such that the metacarpal unit pivots vertically in a first direction relative to the base unit when worn by the user, and the hinge system further movably connecting the metacarpal unit to the base unit when worn by the user, such that the metacarpal unit pivots laterally with respect to the base unit in a second direction substantially transverse to the first direction when worn by the user; and said support member has at least one stop thereon to limit movement of the metacarpal unit relative to the base unit.

9. The orthotic device as recited in claim 8, further comprising:

a support pad on said support member, the support pad being made of a material selected from a group consisting of open cell foam, closed cell foam, cotton, a viscoelastic polymer-gel and an air filled member.

10. The orthotic device as recited in claim 8, wherein said support member includes a plurality of apertures each for receiving a vertical connector therein.

11. The orthotic device as recited in claim 8, wherein said support member and said casing are each made of a material selected from a group consisting of epoxy matrix carbon fiber, moldable carbon fiber, aramid fiber composite material, plastic and thermoplastic material.

12. The orthotic device as recited in claim 8, wherein the hinge system includes a pair of vertical connectors for pivoting the metacarpal unit in the first direction, and a lateral connector for moving the metacarpal unit in the lateral direction.

13. The orthotic device as recited in claim 8, wherein the hinge system further includes a shell extending between the base unit and the metacarpal unit.

14. The orthotic device as recited in claim 8, wherein said hinge system is capable of moving said metacarpal unit to a 45° angle in a vertical extension fashion with respect to the base unit.

15. The orthotic device as recited in claim 8, wherein said hinge system is capable of moving said metacarpal unit to a 150° angle in a vertical, flexing fashion with respect to the base unit.

16. An orthotic device to be worn by a user, comprising:

a base unit having a support member conforming substantially to a forearm of the user;

a metacarpal unit including a casing for positioning on the dorsal surface of the user's hand; and a hinge system connecting said base unit to said metacarpal unit, said hinge system having a shell extending between the base unit and the metacarpal unit, such that the shell pivots vertically in a first direction relative to the base unit when worn by the user, and the hinge system further including a lateral connector for movably connecting the metacarpal unit to the shell when worn by the user, such that the metacarpal unit pivots with respect to the shell laterally in a second direction substantially transverse to the first direction when worn by the user, said hinge system being capable of moving said shell to a 45° angle in a vertical extension fashion with respect to the base unit, and to a 150° angle in a vertical, flexing fashion with respect to the base unit.

17. The orthotic device as recited in claim 16, further comprising:

a support pad on said support member, a fastener extending between said support member and said support pad, and a plurality of apertures in said support member each capable of receiving a vertical connector therein.

18. The orthotic device as recited in claim 16, wherein said support member and said shell each has at least one stop formed thereon to limit extension of the metacarpal unit relative to the base unit.

19. The orthotic device as recited in claim 16, wherein the hinge system includes a pair of vertical connectors for movably connecting the shell to the base unit when worn by the user; and a lateral connector for moveably connecting the metacarpal unit to the shell when worn by the user.

* * * * *